United States Patent [19]

Grollier et al.

[11] Patent Number: 4,876,083
[45] Date of Patent: Oct. 24, 1989

[54] COMPOSITION IN THE FORM OF AN AEROSOL FOAM, BASED ON A POLYMER DERIVED FROM QUATERNIZED CELLULOSE AND AN ANIONIC POLYMER

[75] Inventors: Jean F. Grollier; Christine Dupuis, both of Paris, France

[73] Assignee: L'oreal, Paris, France

[21] Appl. No.: 95,861

[22] Filed: Sep. 14, 1987

[30] Foreign Application Priority Data

Sep. 15, 1986 [LU] Luxembourg .................. 86.585

[51] Int. Cl.$^4$ .................. A61K 7/48; A61K 7/15; A61K 7/42; A61K 7/021
[52] U.S. Cl. .................. 424/47; 424/59; 424/63; 424/73; 424/78; 514/781; 514/945
[58] Field of Search .................. 424/47, 73, 59, 61, 424/63, 78; 514/781, 945

[56] References Cited

U.S. PATENT DOCUMENTS

| | | | |
|---|---|---|---|
| 3,472,840 | 10/1969 | Stone et al. .................. | 260/231 |
| 4,240,450 | 12/1980 | Grollier et al. .................. | 132/7 |
| 4,445,521 | 5/1984 | Grollier et al. .................. | 132/7 |
| 4,761,273 | 8/1988 | Grollier et al. .................. | 424/47 |

FOREIGN PATENT DOCUMENTS

| | | |
|---|---|---|
| 0024161 | 1/1981 | European Pat. Off. . |
| 2383660 | 10/1978 | France . |
| 2098624 | 11/1982 | United Kingdom . |

OTHER PUBLICATIONS

"Performance of UCARE Polymer SR-10", Union Carbide Product Information, Dec. 30, 1985.

Primary Examiner—Ellis P. Robinson
Assistant Examiner—Susan S. Rucker
Attorney, Agent, or Firm—Fleit, Jacobson, Cohn, Price, Holman & Stern

[57] ABSTRACT

Cosmetic composition packaged under pressure in an aerosol device, in the presence of a propellant, characterized in that it contains, in a cosmetically acceptable aqueous medium, at least one quaternary cellulose ether corresponding to the formula:

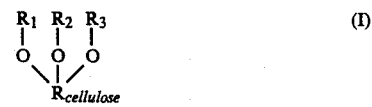

(I)

Rcellulose is a radical of an anhydroglucose unit. in which at least one of the groups $R_1$, $R_2$ or $R_3$ denotes a radical of formula

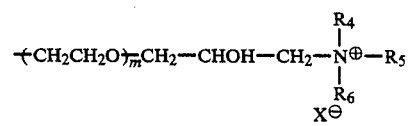

in which m is an integer with a value from 2 to 10, $R_4$, $R_5$ and $R_6$ denote a lower alkyl radical containing 1 to 4 carbon atoms, $X^\ominus$ denotes a cosmetically acceptable anion, the remaining groups $R_1$, $R_2$ or $R_3$ denoting a lower hydroxyalkyl radical containing 1 to 4 carbon atoms, and at least one graft copolymer of vinyl acetate, crotonic acid and polyalkylene glycol, under conditions such that they form, from the device, a stable and firm foam on expansion in air.

13 Claims, No Drawings

COMPOSITION IN THE FORM OF AN AEROSOL FOAM, BASED ON A POLYMER DERIVED FROM QUATERNIZED CELLULOSE AND AN ANIONIC POLYMER

The present invention relates to a new composition based on anionic and cationic polymers, dispensed in the form of a foam from an aerosol device in which the composition is packaged under pressure. The foam thus formed is intended for use in the cosmetic treatment of skin.

Cosmetic compositions which are pressurized in aerosol devices under conditions such that they form a foam at the outlet, are well known and have been used in the treatment of hair or of skin for the past few years.

For the sake of simplicity of the language, such a composition will be called "aerosol foam".

Known foams enable a good distribution of the cosmetic composition on the hair to be achieved and have, in this use, the essential characteristic of being short-lived, i.e. of disappearing very quickly, generally within periods of less than 1 minute after application of the foam to the hair followed by a massage in order to make the foam penetrate.

The present invention relates to compositions intended for use in the cosmetic treatment of skin. "Cosmetic treatment" refers to a treatment which consists, for example, in softening, in making supple, in hardening or in achieving an antigrease or moisturizing effect of the skin.

The foams of the prior art are described more particularly in French patent application No. 2,505,348 of the Applicant Company. Although they have a definite advantage with regard to the treatment of keratin fibres and in particular hair, which advantage results essentially from a combination of anionic and cationic polymers, they have the characteristic of being short-lived, i.e. they disappear very quickly on contact with hair, but are, however, less useful in skin treatment.

In fact, the Applicant Company seeks in particular a cosmetic foam which is not short-lived, intended for skin treatment, highly convenient to apply, easy to spread, which can be used especially as a softening product which enables an emollient film to be formed, especially when it is used as a product for massage.

The Applicant Company has surprizingly discovered that some quaternary cellulose ethers combined with some copolymers of vinyl acetate and crotonic acid led to the formation of a stable, abundant and firm foam.

It should be noted that these quaternary cellulose ethers do not produce stable foam when they are employed alone in the same aerosol device. Moreover, when they are employed alone in the aerosol device, the particular copolymers of vinyl acetate and crotonic acid form an expanded foam which lacks firmness and which is unstable in nature. The foam thus formed by the combination is therefore probably due to a synergistic effect.

Surprizingly, foams thus obtained are pleasant and non-greasy to touch and are particularly suitable for applying to the skin; they may be used in particular as shaving foams, pre-shave or aftershave foams, as suntan foams and treatment foams containing an active product which leaves a smooth, soft and silky skin.

The subject of the invention is therefore a cosmetic composition pressurised in an aerosol device, containing at least one quaternary cellulose ether derivative as will be defined later and a specific copolymer of crotonic acid and vinyl acetate which forms a stable foam on expansion in air.

"Stable foam" means a foam which has a life-span longer than 1 minute after application to the skin. The foam according to the invention is further particularly firm.

Another subject of the invention consists of a method for the cosmetic treatment of skin, which employs such a composition.

Other subjects of the invention will become apparent on reading the description and examples which follow.

The cosmetic composition intended for use in the form of a foam is essentially characterized in that it contains, in a cosmetically acceptable medium, at least one cationic polymer derived from a quaternary cellulose ether corresponding to the formula:

Recellulose is a radical of an anhydroglucose unit in which at least one of the groups $R_1$, $R_2$ or $R_3$ denotes a radical of formula:

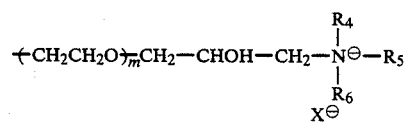

in which m is an integer which has a value from 2 to 10, $R_4$, $R_5$ and $R_6$ denote a lower alkyl radical containing 1 to 4 carbon atoms and preferably methyl, $X^\ominus$ denotes a cosmetically acceptable anion such as $Cl^\ominus$ or $Br^\ominus$, the remaining groups $R_1$, $R_2$ or $R_3$ denoting a lower hydroxyalkyl radical containing 1 to 4 carbon atoms and preferably hydroxyethyl, and at least one graft copolymer of vinyl acetate, crotonic acid and polyalkylene glycol.

The polymer derived from quaternary cellulose ether has a molecular weight of between 100,000 and 3,000,000, and preferably between 200,000 and 800,000 and a viscosity of between 0.1 and 30 Pa.s at 25° C. in a 2% by weight aqueous solution, as determined according to the ASTM D-2364-65 method (Brookfield model LVF, 30 rpm) and preferably between 8 and 12 Pa.s.

The preferred cationic polymer is more particularly the chloride of the ω-cellulose ether of α-[2-hydroxy-3-(trimethylammonio)propyl]- -hydroxypoly(oxy-1,2-ethanediyl), and especially the product sold under the name UCARE ® polymer SR 10 by UNION CARBIDE.

Graft copolymers of vinyl acetate, crotonic acid and polyalkylene glycol are described in German Pat. No. 1,077,430. Their viscosity, in a 5% solution in dimethylformamide at 35° C., is greater than 0.0010 Pa.s, generally between 0.0015 and 0.015 Pa.s and more particularly between 0.0020 and 0.010 Pa.s.

The particularly preferred copolymer of vinyl acetate, crotonic acid and polyalkylene glycol is a graft copolymer of vinyl acetate, crotonic acid and polyethylene glycol and more particularly the graft copolymer prepared starting with 400 parts of vinyl acetate, 32 parts of crotonic acid and 40 parts of polyethylene glycol with a molecular weight of 4,000. Among these copolymers, there may be mentioned the product sold under the name ARISTOFLEX A by HOECHST; its viscosity, in a 5% solution in dimethylformamide at 35° C., is between 0.0025 and 0.0028 Pa.s.

The Applicant Company has observed that this combination had a synergistic effect with regard to an aerosol foam formation and with regard to the stability of the latter.

The quaternary cellulose ether polymer is present in the compositions according to the invention in proportions of between 0.3 and 5% by weight relative to the total weight of the composition and preferably between 0.3 and 2%, and more particularly between 0.6 and 1% by weight.

The graft copolymer of vinyl acetate, crotonic acid and polyalkylene glycol is preferably employed in the compositions according to the invention in proportions from 0.1 to 3% by weight relative to the total weight of the composition and preferably from 0.1 to 1% and more particularly from 0.3 to 0.6%.

The ratio by weight of the quaternary cellulose ether as defined above to the vinyl acetate/crotonic acid/polyalkylene glycol copolymer which is also defined above, is preferably greater than or equal to 1, and in particular between 1 and 10.

The compositions according to the invention are aqueous compositions with a pH preferably between 6 and 9, and in particular between 7.5 and 8.5. The pH is adjusted with alkalinizing or acidifying agents which are well known in cosmetics.

The cosmetically acceptable medium consists of water or a mixture of water and alcohol. The alcohols are more particularly chosen from amongst $C_1-C_4$ lower alkanols such as ethyl or isopropyl alcohol. The proportions of alcohol may range up to 40% by weight relative to the total weight of the composition.

The compositions according to the invention may contain any other adjuvant which is cosmetically acceptable and which can be used in skin treatment. Perfumes, colouring agents which have the role of colouring the composition itself or the skin, preservatives, sequesterants, antigrease agents, antiseborrheic agents, silicones, softeners, sunscreens, peptizing agents, emollients, humectants or vitamins may in particular be employed. Each of these different adjuvants may be present in proportions ranging between 0.01 and 10% by weight relative to the total weight of the composition.

These compositions may optionally contain anionic, nonionic, amphoteric or cationic surfactants or mixtures thereof, preferably in proportions of less than 10% and in particular less than 7%.

These different constituents must be present in proportions such that they do not have a deleterious effect on the foam, such as preventing the formation thereof.

These compositions are packaged under pressure in aerosol devices which are known in themselves, in the presence of propellant gases which are generally present in proportions not exceeding 25% relative to the total weight of the composition and preferably 15%.

It is possible to employ, as propellant gases, carbon dioxide, nitrogen, nitrous oxide, volatile hydrocarbons such as butane, isobutane and propane and mixtures thereof, halogenated, chlorinated and/or fluorinated hydrocarbons which cannot be hydrolyzed, such as compounds sold under the name FREON by DU PONT DE NEMOURS, and more particularly fluorochlorohydrocarbons such as dichlorodifluoromethane or dichlorotetrafluoroethane. These propellants may be employed alone or in the form of mixtures such as, for example, the mixture "FREON 114/FREON 12" in proportions of beteen 40:60 and 80:20.

Another subject of the invention also consists of a cosmetic treatment foam obtained by dispensing the composition under pressure, defined above, from an aerosol device.

The following examples are intended to illustrate the invention without being, however, limiting in nature.

EXAMPLE 1

A skin softening foam with the following composition is prepared:

| | |
|---|---|
| Ucare Polymer SR 10 | 0.6 g AS |
| Aristoflex A | 0.3 g AS |
| Ethyl alcohol qs | 20° |
| Preservative, perfume qs | |
| 2-Amino-2-methyl-1-propanol qs pH | 7.5 |
| Water qs | 100.0 g |

This composition is pressurized in an aerosol device, in the following proportions:

| | |
|---|---|
| Composition | 90 g |
| Propellants: | |
| Freons 114/12 (43/57) | 10 g |

An application of this well expanded and stable foam, not followed by rinsing, makes the skin smooth and soft.

EXAMPLE 2

A skin softening foam with the following composition is prepared:

| | |
|---|---|
| Ucare Polymer SR 10 | 0.5 g AS |
| Aristoflex A | 0.5 g AS |
| Ethyl alcohol qs | 20° |
| 2-Amino-2-methyl-1-propanol qs pH | 7.5 |
| Preservative, perfume qs | |
| Water qs | 100.0 g |

This composition is pressurized in an aerosol device, in the following proportions:

| | |
|---|---|
| Composition | 90 g |
| Propellants: | |
| Freons 114/12 (43/57) | 10 g |

On application to the skin, this well expanded and stable foam makes it smooth and soft.

EXAMPLE 3

A softening foam for greasy skin, with the following composition is prepared:

| | |
|---|---|
| Ucare Polymer SR 10 | 1.0 g AS |
| Aristoflex A | 0.6 g AS |
| Poly(beta-alanine) | 1.0 g |
| Isopropyl alcohol qs | 10° |
| 2-Amino-2-methyl-1-propanol qs pH | 8.5 |
| Perfume, preservative, colouring agent qs | |
| Water qs | 100.0 g |

This composition is pressurized in an aerosol device, in the following proportions:

| Composition | 90.0 g |
|---|---|
| Propellants | 10.0 g |
| Freons F 114/F 12 (43/57) | |

EXAMPLE 4

A skin softening foam with the following composition is prepared:

| Ucare Polymer SR 10 | 2.0 g AS |
|---|---|
| Aristoflex A | 0.6 g AS |
| 2-Hydroxy-4-methoxybenzophenone-5-sulphonic acid (Uvinul MS 40) | 2.0 g |
| 2-Amino-2-methyl-1-propanol qs pH | 8.0 |
| Water qs | 100.0 g |

This composition is pressurized in an aerosol device, in the following proportions:

| Composition | 90.0 g |
|---|---|
| Propellants | 10.0 g |
| Freons F 114/F 12 (43/57) | |

EXAMPLE 5

A skin softening and moisturizing foam with the following composition is prepared:

| Ucare Polymer SR 10 | 2.5 g AS |
|---|---|
| Aristoflex A | 0.5 g AS |
| Glycerine | 2.0 g |
| 2-Amino-2-methyl-1-propanol qs pH | 8.5 |
| Water qs | 100.0 g |

This composition is pressurized in an aerosol device, in the following proportions:

| Composition | 90.0 g |
|---|---|
| Propellants | 10.0 g |
| Freons F 114/F 12 (43/57) | |

EXAMPLE 6

A skin softening foam with the following composition is prepared:

| Ucare Polymer SR 10 | 3.0 g AS |
|---|---|
| Aristoflex A | 0.3 g AS |
| Vitamin F | 0.5 g |
| 2-Amino-2-methyl-1-propanol qs pH | 8.5 |
| Ethyl alcohol qs | 10° |
| Perfume, preservative, colouring agent qs | |
| Water qs | 100.0 g |

This composition is pressurized in an aerosol device, in the following proportions:

| Composition | 90.0 g |
|---|---|
| Propellants | 10.0 g |
| Freons F 114/F 12 (43/57) | |

We claim:

1. Cosmetic composition for use on skin packaged under pressure in an aerosol device, in the presence of a propellant, containing in a cosmetically acceptable medium between 0.3 and 5% by weight relative to the total weight of the composition of a quaternary cellulose ether corresponding to the formula:

$R_{cellulose}$ is a radical of an anhydroglucose unit in which at least one of the groups $R_1$, $R_2$ or $R_3$ denotes a radical of formula

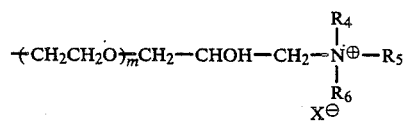

in which m is an integer with a value from 2 to 10, $R_4$, $R_5$ and $R_6$ denote a lower alkyl radical containing 1 to 4 carbon atoms, $X^\ominus$ denotes a cosmetically acceptable anion, the remaining groups $R_1$, $R_2$ or $R_3$ denoting a lower hydroxyalkyl radical containing 1 to 4 carbon atoms, and a graft copolymer of vinyl acetate, crotonic acid and polyalkylene glycol, under conditions such that they form, from the device, a stable foam on expansion in air which has a life-span longer than 1 minute after application to the skin.

2. Compositions according to claim 1, wherein the quaternary cellulose ether is the chloride of the ω-cellulose ether of α-[2-hydroxy-3-(trimethylammonio)-propyl]-ω-hydroxypoly(oxy-1,2-ethanediyl).

3. Composition according to claim 1 wherein the graft copolymer of vinyl acetate, crotonic acid and polyalkylene glycol is a vinyl acetate/crotonic acid/polyethylene glycol copolymer.

4. Composition according to claim 1, wherein the quaternary cellulose ether (1) is present in proportions of between 0.3 and 2% by weight relative to the total weight of the composition.

5. Composition according to claim 1, wherein the graft copolymer of vinyl acetate, crotonic acid and polyalkylene glycol is present in proportions of between 0.1 and 3% by weight relative to the total weight of the composition.

6. Composition according to claim 1, wherein the ratio by weight of the quaternary cellulose ether to the vinyl acetate/crotonic acid/polyalkylene glycol copolymer is greater than or equal to 1.

7. Composition according to claim 1, wherein the cosmetically acceptable medium is an aqueous medium or a mixture of water and alcohols selected from the group consisting of lower alkanols.

8. Composition according to claim 1, wherein the alcohol is present in proportions of less than or equal to 40% by weight relative to the total weight of the composition.

9. Composition according to claim 1, further containing perfumes, colouring agents which have the role of colouring the composition or the skin, preservatives, sequesterants, antigrease agents, antiseborrheic agents, silicones, softening agents, sunscreens, peptizing agents, humectants, emollients, vitamins or anionic, nonionic, cationic or amphoteric surfactants or the mixtures thereof.

10. Composition according to claim 1 wherein the propellant is employed in proportions not exceeding 25% relative to the total weight of the composition and that it is selected from the group consisting of carbon dioxide, nitrogen, nitrous oxide, volatile hydrocarbons such as butane, isobutane, propane and mixtures thereof and halogenated, chlorinated and/or fluorinated, hydrocarbons which cannot be hydrolyzed.

11. Cosmetic treatment foam obtained by dispensing the composition under pressure according to claim 1, from an aerosol device.

12. Method for the cosmetic treatment of skin, comprising the application to the skin of a foam as defined in claim 11.

13. Composition according to claim 1, wherein the graft copolymer of vinyl acetate, crotonic acid and polyalkylene glycol is present in proportions of between 0.1 and 1% by weight relative to the total weight of the composition.

* * * * *